(12) United States Patent
Erickson

(10) Patent No.: US 6,361,521 B1
(45) Date of Patent: Mar. 26, 2002

(54) NASAL IRRIGATION SYSTEM

(76) Inventor: Grant C. Erickson, P.O. Box 1201, Grantsville, UT (US) 84029

( * ) Notice: Subject to any disclaimer, the term of this patent is extended or adjusted under 35 U.S.C. 154(b) by 0 days.

(21) Appl. No.: 09/387,630

(22) Filed: Aug. 31, 1999

Related U.S. Application Data

(63) Continuation-in-part of application No. 09/185,043, filed on Nov. 3, 1998, now abandoned.

(51) Int. Cl.[7] ........................ A61M 31/00; A61M 5/178; A61M 11/00; A61N 1/30
(52) U.S. Cl. ........................ 604/37; 604/19; 604/36; 604/294; 604/500; 128/200.22
(58) Field of Search ........................ 604/1–2, 19, 36, 604/37, 48, 29, 500; 128/200.14, 200.22, 200.23, 200.28; 222/72, 633, 92–96, 204, 527, 206–213, 528, 530, 542

(56) References Cited

U.S. PATENT DOCUMENTS

| | | |
|---|---|---|
| 1,658,801 A | 2/1928 | Condren |
| 3,516,407 A | 6/1970 | Ruggero |
| 4,994,076 A * | 2/1991 | Guss ........................ 606/236 |
| 5,601,594 A | 2/1997 | Best |
| 5,713,855 A | 2/1998 | Shippert |
| 5,713,914 A | 2/1998 | Lee |
| 5,921,233 A * | 7/1999 | Gold et al. ............ 128/200.22 |
| 5,921,998 A | 7/1999 | Tano et al. |

\* cited by examiner

Primary Examiner—Kim M. Lewis
(74) Attorney, Agent, or Firm—Morriss. Bateman, O'Bryant & Compagni

(57) ABSTRACT

A system for safely irrigating nasal and sinus cavities using a portable and reusable device which can be conveniently coupled to a fluid container, wherein the system includes an adapter end for coupling to the fluid container, an insertion end which directs fluid from the fluid container into the nasal and sinus cavities while preventing damage thereto by preventing insertion of the insertion end into the nasal cavities beyond a predetermined length, and a curved section of tubing which is coupled to the adapter end and the insertion end, wherein the curved section of tubing makes the user hold the fluid container in a correct position for directing solution from the fluid container into the nasal and sinus cavities.

20 Claims, 9 Drawing Sheets

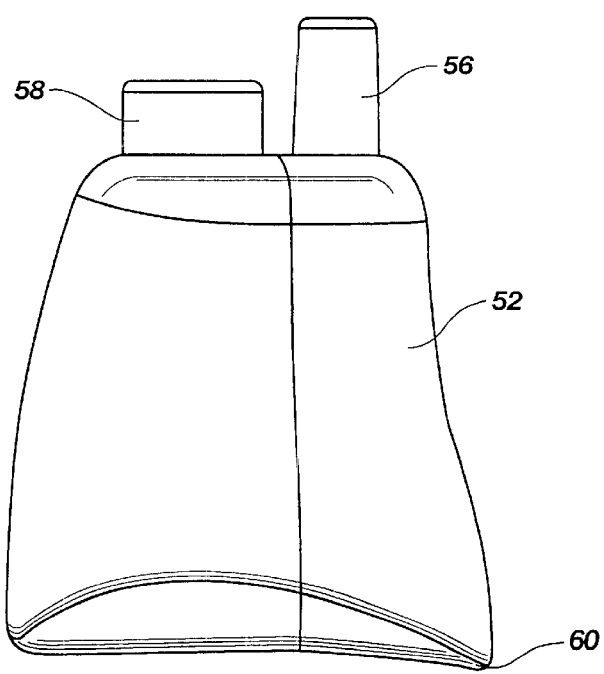
*Fig. 8B*
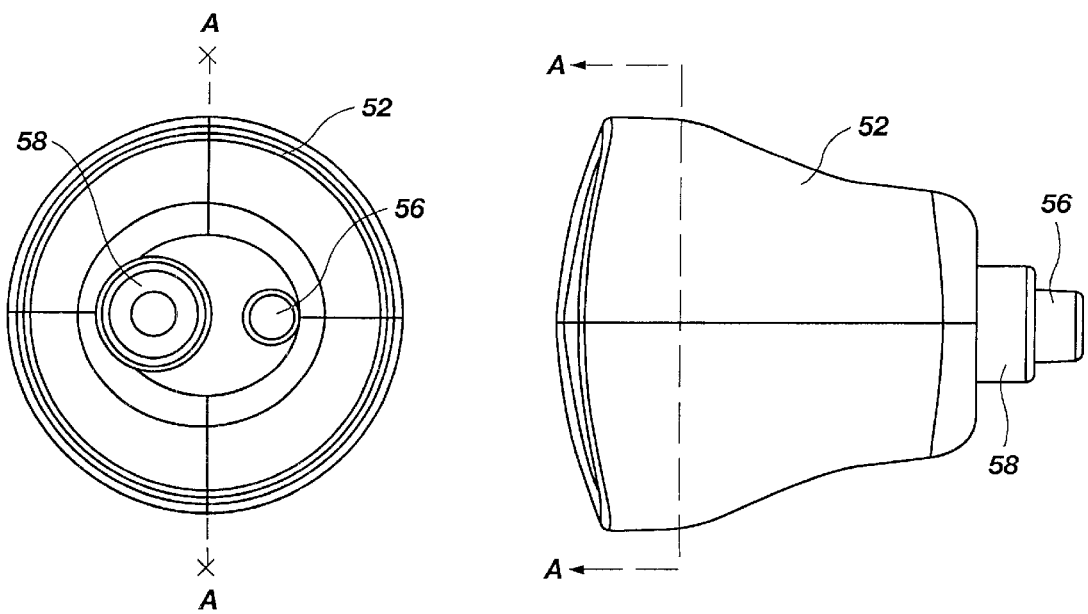
*Fig. 8D*  *Fig. 8C*

NASAL IRRIGATION SYSTEM

CROSS REFERENCE TO RELATED APPLICATIONS

This document claims priority to and is a Continuation-in-part application of U.S. patent application Ser. No. 09/185,043, filed Nov. 3, 1998 now abandoned.

BACKGROUND

1. The Field of the Invention

This invention relates generally to medical devices for irrigation of sensitive sinus tissue. More specifically, the invention relates to a reusable and portable device for irrigating sinus tissue in the sinus cavity, wherein the device can be conveniently adapted for use with a water bottle as a fluid source, and used in any convenient location.

2. The State of the Art

The need to irrigate sinus and nasal tissue is commonly a result of injury or surgery to a portion thereof. Treatment of the sinus cavities often consists of irrigation using a saline solution or other sterile and therapeutic fluid to thereby assist in the healing process and increase the comfort of the patient.

The state of the art in sinus irrigation systems is characterized by devices which, if used improperly, can easily cause severe damage to sensitive membranes and tissues. There are several disadvantageous features of the device which can allow the damage to occur. As shown in FIG. 1, some devices have a relatively long wand or handle 2 which, unfortunately, can be inserted further than is necessary into the sinus cavities. In addition, the device is powered by an electric pump 4 which either does not allow for regulation of the flow of fluid into the sinus cavities, or is difficult and non-intuitive to control. Furthermore, because the device is electric, it is not very portable.

Accordingly, what is needed is a convenient way to irrigate tissue in the sinus cavities which does not require electrically powered, bulky, potentially harmful, and expensive equipment. Furthermore, it would be a further improvement over the state of the art to provide a system for sinus irrigation which can be used with a fluid container having an attachment port whose shape, size and thread spacing is consistent with a commonly found industry standard, such that the system can be used without difficulty in many locations where water bottles can be obtained. Finally, it would be another improvement to provide an irrigation system which is adapted to be coupled directly to a portion of a commonly found sport cap assembly after easy removal of a portion thereof.

OBJECTS AND SUMMARY OF THE INVENTION

It is an object of the present invention to provide a portable system for directing a solution in a container to a nostril to thereby irrigate sinus tissue in the sinus cavities.

It is another object to provide the system with an irrigation port which is coupled to a container, wherein the irrigation port directs fluid from the container out through the irrigation port.

It is another object to provide the irrigation port which is adapted to be comfortably and only partially inserted into a nostril.

It is another object to provide the irrigation port which prevents insertion into the nostril beyond a predetermined length of insertion.

It is another object to provide the irrigation port with a cap adapter which is coupled to an industry standard sports cap which is commonly used on containers of fluid.

It is another object to provide the irrigation port with a cap adapter which is already coupled to a sports cap which includes screw threads which are designed for coupling to the industry standard opening of commonly used fluid containers.

It is another object to provide the irrigation port with a means for preventing fluid flow out through the irrigation port, such that the system will not spill solution from the container when it is desirable to move the system, or application of solution is complete.

It is another object of the present invention to provide a portable system for use as a feminine hygiene product which is able to direct a fluid to a desired location to thereby enable irrigation thereof.

It is another object to provide a portable eye washing system, wherein the insertion end is replaced by an end designed to fit up against a person's face and around an eye, such that fluid from a container can be directed against the eye to thereby flush it of contaminants in an emergency.

It is another object to provide a portable system which can be coupled to a container of fluid to thereby enable the fluid to be directed into the mouth of a person who is wearing headgear which otherwise obstructs access of a drinking container.

In a preferred embodiment, the present invention is a system for safely irrigating nasal and sinus cavities using a portable and reusable device which can be conveniently coupled to a fluid container, wherein the system includes an adapter end for coupling to the fluid container, an insertion end which directs fluid from the fluid container into the nasal and sinus cavities while preventing damage thereto by preventing insertion of the insertion end into the nasal cavities beyond a predetermined length, and a curved section of tubing which is coupled to the adapter end and the insertion end, wherein the curved section of tubing makes the user hold the fluid container in a correct position for directing solution from the fluid container into the nasal and sinus cavities.

In a first aspect of the invention, the system is coupled to a fluid container by snapping the adapter end onto a portion of a sports cap after removal of a portion thereof.

In a second aspect of the invention, the system includes an adapter end which changes from a closed position to an open position by pulling on a top portion thereof, thereby enabling the system to prevent spilling of solution when not in use.

In a third aspect of the invention, the curved tubing causes a user of the system to naturally hold the fluid container in an up-ended condition, suitable for delivering solution from the fluid container and into the sinus cavities, In a fourth aspect of the invention, the insertion end includes a flared barrier which prevents insertion of the insertion end into a nostril beyond the flared barrier, thereby preventing injury to sensitive tissue within the nasal and sinus cavities which could otherwise be scraped by the insertion end.

In a fifth aspect of the invention, the irrigation system is reusable, and made from a material which allows for the irrigation system to be sterilized.

In a sixth aspect of the invention, the irrigation system can include an adapter end which includes a portion of a sports cap assembly, so that the irrigation system can be screwed directly onto a fluid container which does not have a sport cap assembly thereon, but has the screw threads for use therewith.

In a seventh aspect of the invention, the insertion end can be replaced with a variety of differently shaped insertion ends.

In an eighth aspect of the invention, an insertion end is provided which is suitable for use as a feminine hygiene product for purposes of irrigation.

In a ninth aspect of the invention, an insertion end is replaced by a cupping shape designed to be pressed against a person's face and around an eye to enable the eye to be flushed of contaminants.

These and other objects, features, advantages and alternative aspects of the present invention will become apparent to those skilled in the art from a consideration of the following detailed description taken in combination with the accompanying drawings.

BRIEF DESCRIPTION OF THE DRAWINGS

FIG. 8B is a side elevational view of the cupping shape used for flushing an eye as shown in FIG. 8A.

FIG. 8C is a side elevational view of the cupping shape used for flushing an eye as shown in FIG. 8B, and shown along the lines A—A.

FIG. 8D is a side elevational view of the complete eye flushing system, which shows the system in relation to a person's eye, and an attached container of fluid.

DETAILED DESCRIPTION OF THE INVENTION

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow.

The presently preferred embodiment of the invention is a system which enables a user to safely and conveniently irrigate sinus cavities without risk of injuring sensitive sinus tissues. Furthermore, the system is inexpensive, portable, and is easily attached to the most common coupling end of water bottles, known as a sports cap.

Figure 1:
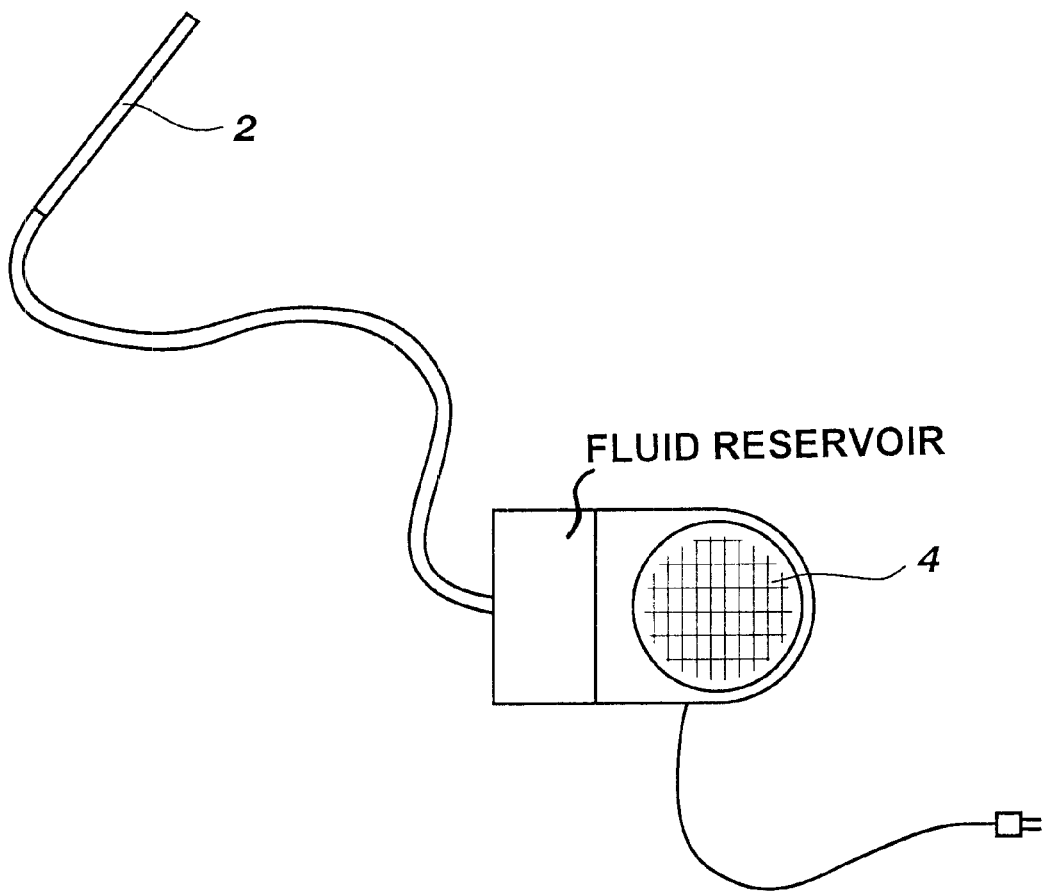
FIG. 1 is a perspective illustration of an irrigation system as taught in the prior art.
Figure 2:
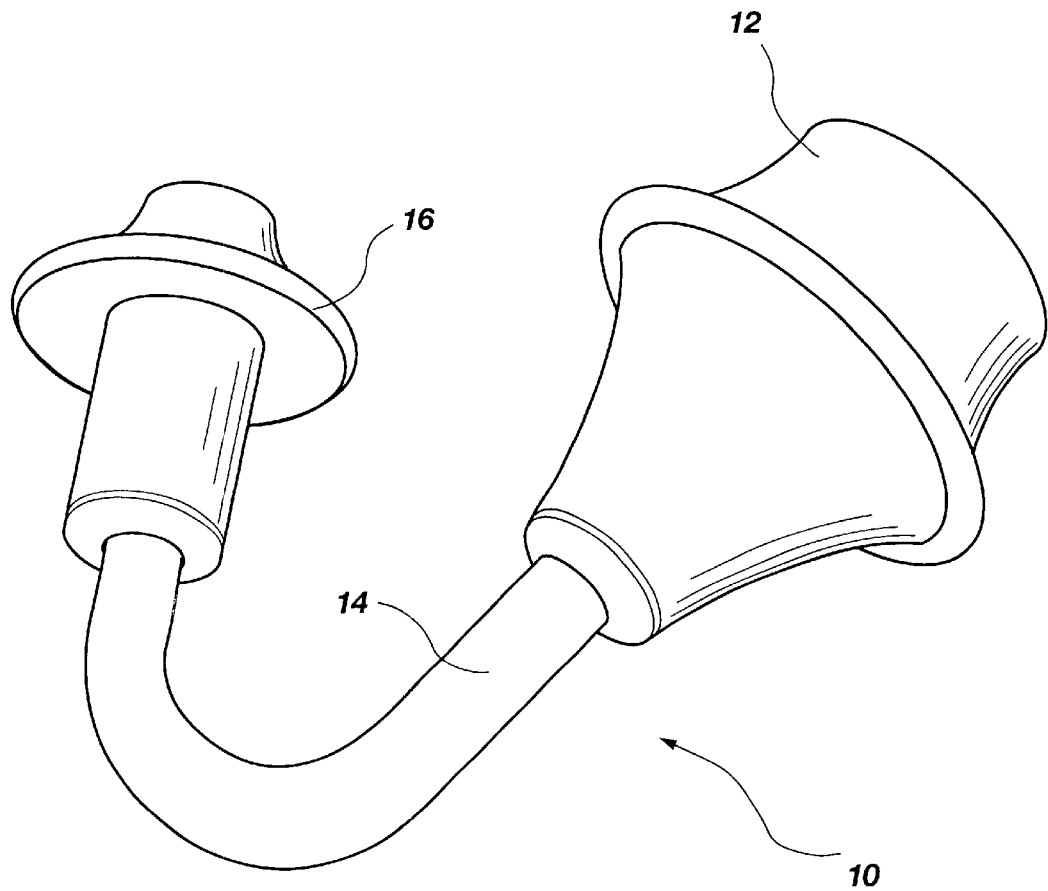
FIG. 2 is a perspective view of the invention which is constructed in accordance with the standards of the presently preferred embodiment.

FIG. 2 is a perspective view of the presently preferred embodiment. The components of the system 10 include a cap adapter 12, a curved tube 14, and an irrigation port or tip 16. The nature and function of each component of the system 10 will now be described in sufficient detail to enable the system to be utilized as intended.

Beginning with the cap adapter 12, this portion of the system is what makes it so adaptable and portable. In other words, the cap adapter 12 is designed to mate with sports caps which have become so ubiquitous in the fluid container industry. The function of the sports cap is to provide convenient access to a fluid in a container. The sports cap is convenient because the user is able to easily pop it open, dispense a fluid, and then reseal to keep the fluid from spilling.

Figure 3:
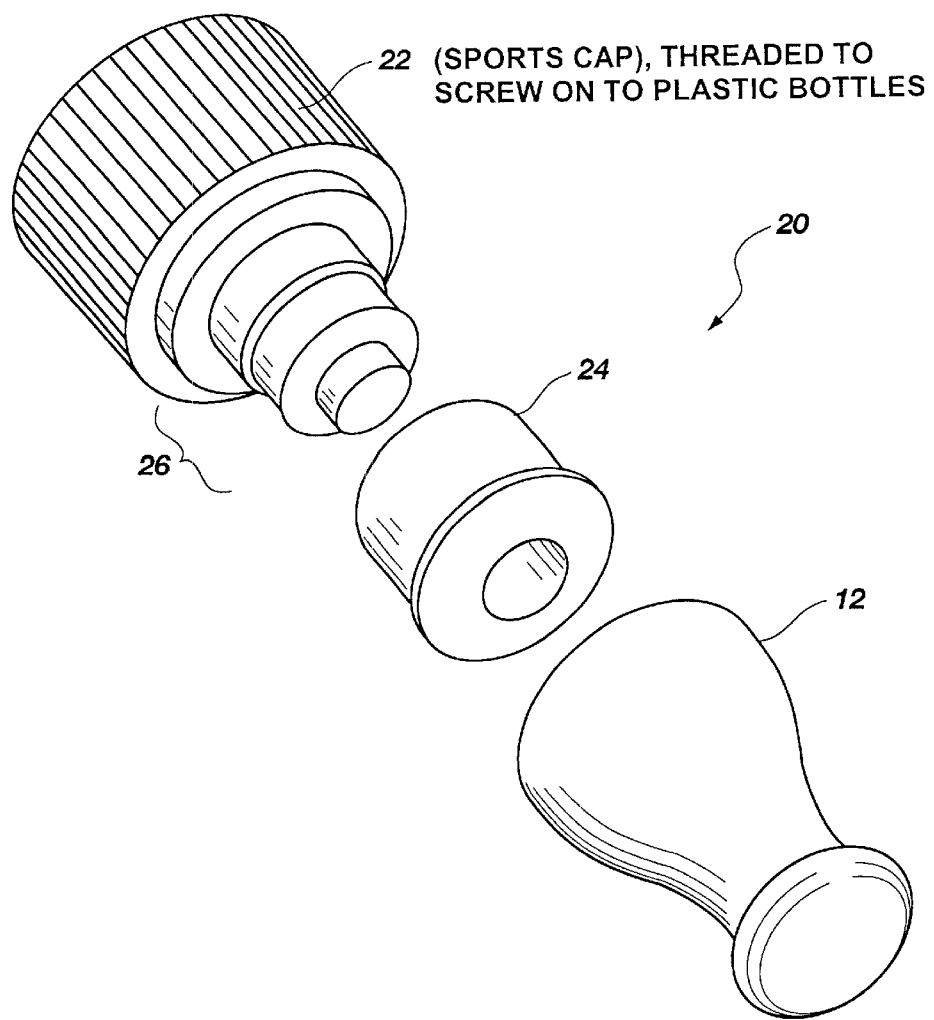
FIG. 3 is a perspective view of a sports cap assembly having a base portion which is the sports cap, and a top portion which is the cap stopper. The figure also illustrates the cap adapter of the preferred embodiment.

FIG. 3 is a perspective view of a sports cap assembly 20. The sports cap assembly is comprised of a the sports cap 22 and a cap stopper 24. The cap stopper 24 snaps onto a neck portion 26 of the sports cap 22. Once it is snapped on, the cap stopper 24 can slide up and down the neck portion 26, thereby opening and closing the sports cap assembly 20, respectively.

The preferred embodiment is designed to be coupled to the sports cap 22. In order to make this connection, it is necessary to remove the cap stopper 24 from the sports cap 22. The cap stopper 24 will lift off of the neck portion 26 if sufficient force is applied. Once the cap stopper 24 is removed, the cap adapter 12 snaps on to the neck portion 26 of the sports cap 22 in the same manner as the cap stopper 24. Essentially, the cap adapter 12 replaces the cap stopper 24 and functions in the same manner. However, as FIG. 3 makes it evident, the cap adapter 12 is longer than the cap stopper 24. The additional length is necessary to provide a means for attaching the curved tube 14.

Figure 4:
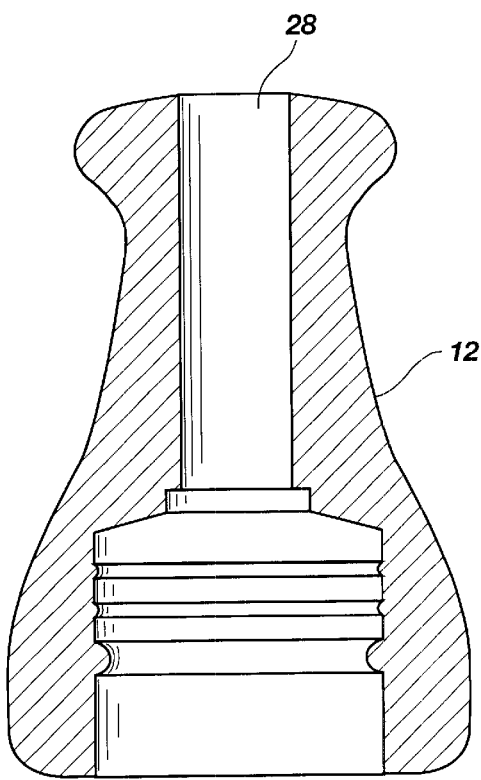
FIG. 4 is a cross-sectional profile view of the cap adapter, illustrating the internal structure which illustrates how solution flows therethrough.

FIG. 4 is a cross-sectional profile view of the cap adapter 12. The interior of the cap adapter 12 appears the same as an interior of the removed cap stopper 24. However, the cap adapter 12 includes a relatively long and straight tube or aperture 28 therethrough. The aperture 28 is designed to mate in sliding engagement with a straight portion of the curved tube 14. In other words, one of the straight ends of the curved tube slides into the aperture 28 of the cap adapter 12. The diameter of the aperture 28 is designed such that the straight portion of the curved tube 14 fits relatively tight so that no other means of securing the curved tube 14 to the cap adapter 12 is necessary. There is sufficient friction between the components to keep them in place.

The last component of the irrigation system 10 is the irrigation tip 16. The irrigation tip 16 is also designed to be coupled to a straight end of the curved tube 14.

Figure 5:
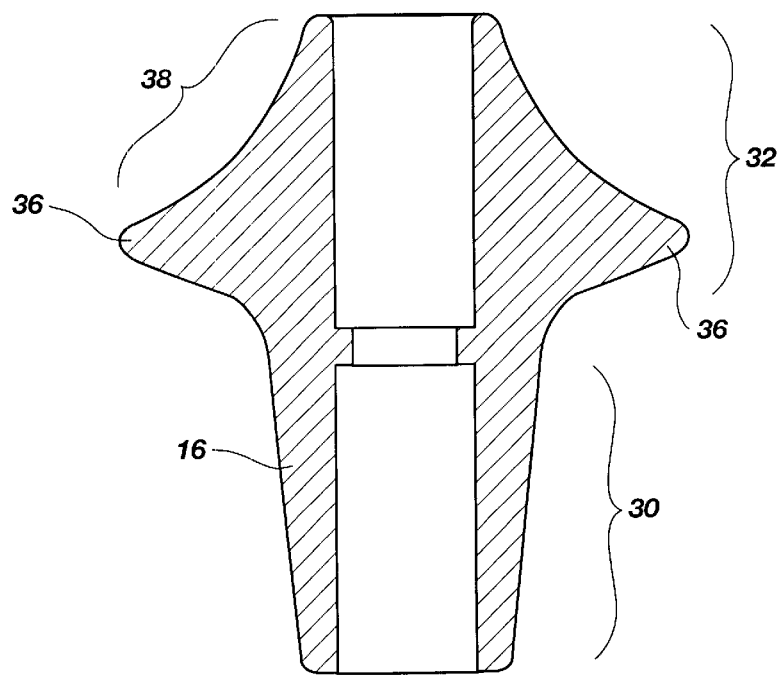
FIG. 5 is a cross-sectional profile view of the irrigation tip, illustrating the internal structure which illustrates how solution flows therethrough.

FIG. 5 is a cross-sectional profile view of the irrigation tip 16. A bottom portion 30 is designed to mate in sliding engagement with another straight end of the curved tube 14. Likewise, friction is also sufficient to keep the curved tube 14 and the irrigation tip 16 coupled to each other during normal use. A top portion 32 is an aperture 34 through which fluid leaves the irrigation tip 16.

One of the most advantageous features of the irrigation tip 16 is a flared barrier 36 at the aperture end. The flared barrier 36 is smooth and gradually curved. It is also sufficiently wide in diameter so as to prevent insertion of the irrigation tip 16 into a nostril farther than the flared barrier 36. In this manner, damage by accidental insertion of the irrigation tip too far into the nasal passage is prevented, thereby protecting sensitive sinus tissue.

The gradual curve 38 of the irrigation tip 16 also generally prevents misdirecting the flow of fluid in any other direction than straight into the nasal passage.

It is observed that the presently preferred embodiment shown in FIG. 4 includes three components. However, in a preferred alternative embodiment, the sports cap 22 shown in FIG. 4 can be part of the irrigation system.

It is also noted that in another alternative embodiment, more than one cap adapter 12 can be provided in the irrigation system 10. This would allow the irrigation system 10 to work with a variety of less common sports cap assemblies. This may be important depending on the country in which the irrigation system 10 is being used, or when a particular type of non-standard container is used in a region or in a particular industry. For example, the medical industry may provide a saline solution in a bottle which has an opening which does fit the industry standard sports cap assembly as shown in FIG. 3.

Having described the components of the presently preferred embodiment, it is useful to review operation and proper use of the irrigation system. A user first acquires a container of the necessary fluid. For the intended purposes of the invention, it is generally assumed that the fluid is a sterile solution, such as medical quality saline. It is generally not a feature of the invention how the sterile solution is prepared. Rather, it is assumed that the proper sterile solution has been acquired and that it will render the desired therapeutic results when properly used.

Another assumption of the present invention is that a container to which the preferred or alternative embodiments can be attached is also provided. In other words, the container might come with a sports cap assembly 20 as shown in FIG. 3. However, the container could also come with some type of removable seal which is disposed on top of a threaded opening, wherein the threaded opening is designed for receiving a sports cap assembly 20. Advantageously, the sports cap assembly 20 is either found on or will fit most water bottles that are commonly sold on the market today. In other words, the threaded opening is an industry standard which is ready for use with industry standard sports cap assemblies 20.

It will be assumed that a container has been acquired which contains the desired medical quality fluid, such as saline, which can be applied to the sinus cavities. Assume that the bottle has a sport cap assembly 20 thereon. The container is held upright, and the cap stopper 24 is removed from the neck portion 26 of the sports cap 22.

Figure 6:
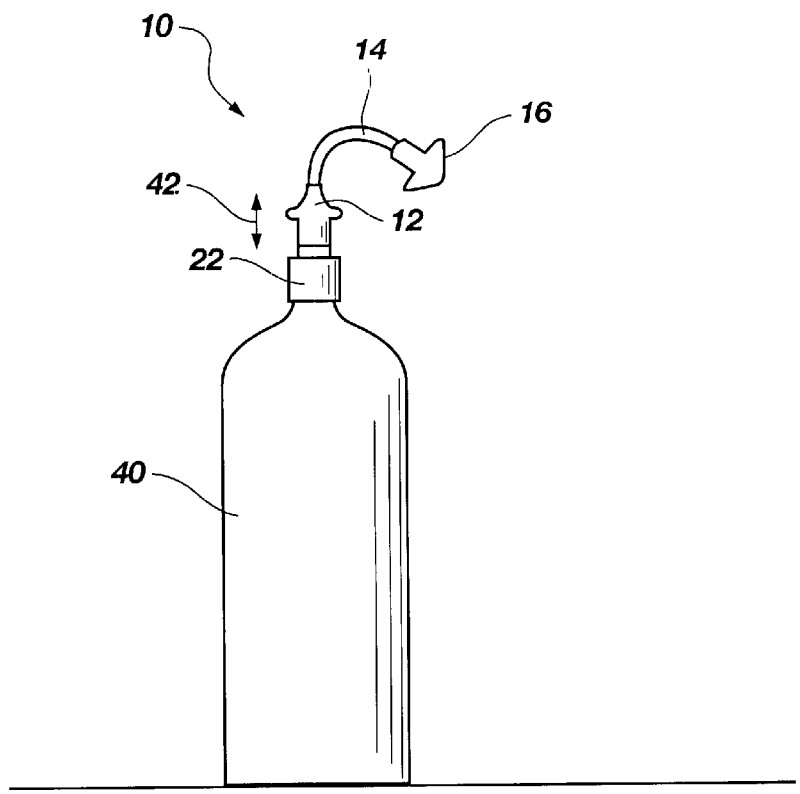
FIG. 6 is a profile view of a container which is coupled to the irrigation system, when the container is in an upright position, and the cap adapter is extended, making the irrigation system ready for use.

FIG. 6 is a profile view of the container 40 which is coupled to the irrigation system 10. The irrigation system is coupled to the sports cap 22 by snapping the irrigation system onto the neck portion (not shown) of the sports cap.

The cap adapter 12 is then free to slide up and down on the neck portion as indicated by arrows 42. When the cap adapter 12 is pulled into an extended position relative to the container 42, fluid within the container can flow through the curved tube 14 and out of the irrigation tip 16.

Figure 7:
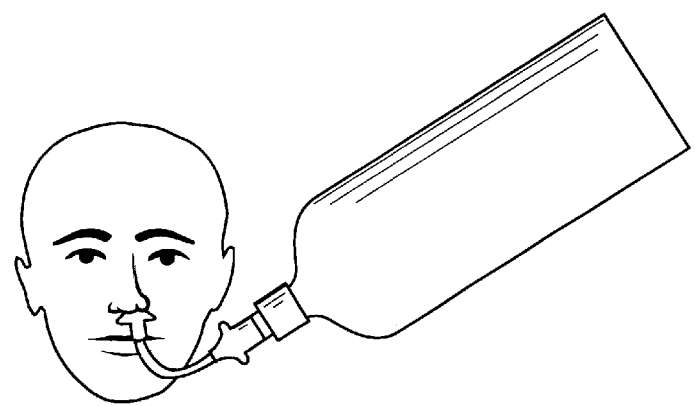
FIG. 7 is a perspective drawing of a user who is holding the irrigation system and container in the proper position for use.

When the irrigation system has been coupled to the container 42 and the user is ready to apply the solution, the irrigation tip 16 is pressed against a nostril. This requires the user to turn and hold the container 42 in the position shown in FIG. 7. The rate of flow of solution out of the container and into the sinus cavities is controlled by applying pressure to the container 42. In other words, the user squeezes the container 42 to get the solution into the sinus cavities.

It is observed that another advantageous feature of the present invention is the ability to very easily control the amount of solution which is directed into the sinus cavities. The user is intuitively able to determine how much pressure should be applied to the compressible container to maintain a gentle flow of solution because pressure is being applied to the container by the user's hands. This is in distinct contrast to the electrical pumping system of the prior art where the rate of flow is controlled by a control switch or knob.

The present invention is constructed of commonly available and inexpensive materials. In the preferred embodiment, the cap adapter 12, the curved tube 14, and the irrigation tip 16 are molded from autocleaveable plastic, such as polyproplynen or polyethylene. However, any material is suitable which has the characteristics of being sterilizeable, and able to hold its shape. It is also desirable, but not required, that the curve tube 14 flex in order to prevent breaking. Likewise, if the sports cap is part of the irrigation system, it should be constructed from the same materials. However, it should be recognized that any suitable form of constructing the components is acceptable and within the scope of the invention.

It is noted that the curved tube 14 is shown having a bend somewhere along its length. As shown, the bend enables more convenient access of an applicator end, and more advantageous handling of a connected fluid reservoir. In one embodiment, it is preferred that the curved tube have an angle of at least 120 degrees. In another embodiment, the bend in the curved tube 14 should be between 45 and 90 degrees.

Another advantage of the embodiments described above is that the cap adapter 12 and the injection tip 16 can be replaced with suitable alternatives, depending upon the application. For example, it may be desirable to have an injection tip with a smaller hole. This could serve the purposes of decreasing the rate of fluid flow.

It is noted that it is important not to inhale when the solution is being directed into the sinus cavities.

It is also noted that because the embodiments above describe separate components, any of the components which have become damaged can be easily replaced. However, it is also a feature of the present invention that the entire irrigation system can be manufactured as a single unit. In this alternative embodiment, the present invention is formed in a single mold. While not as versatile, this construction can decrease manufacturing costs, while still obtaining the desired form and function of the separate components. Nevertheless, the entire irrigation assembly would be disposed of when damaged.

Having described the embodiments of the nasal irrigation system, it is another advantageous feature of the present invention to provide different injection tips. Different injection tips enable the invention to be adaptable to different applications. In other words, different shapes of tips enable the invention to direct fluids in different ways.

Figure 8A:
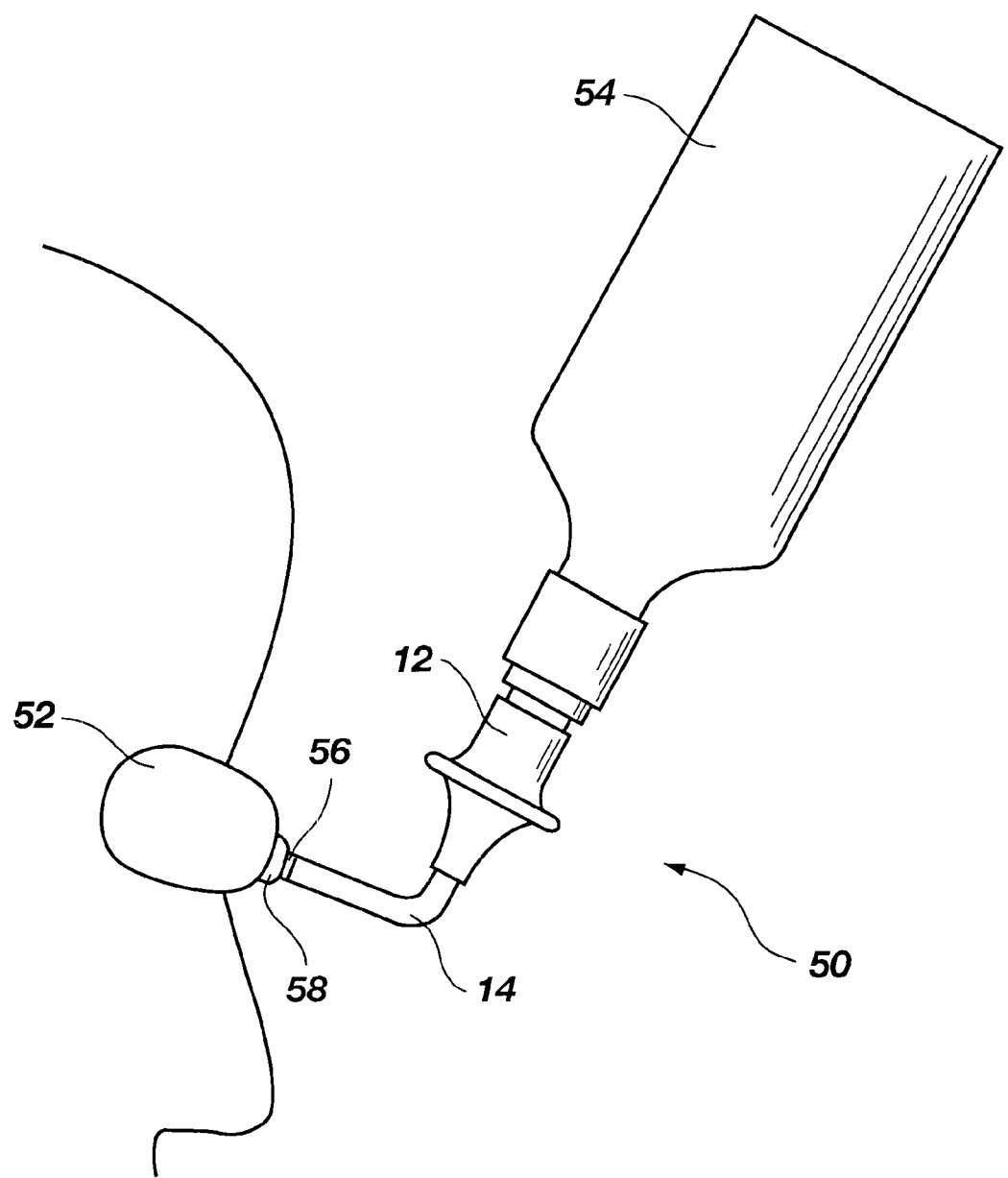
FIG. 8A is a top elevational view of an alternative embodiment of the invention, where an insertion end is replaced by a cupping shape which is designed to enable a person's eye to be flushed of contaminants.

For example, another alternative embodiment is shown in FIG. 8A. FIG. 8A shows a different type of end piece that is used in place of the irrigation tip 16 of the nasal irrigation system 10 (see FIG. 2). This new tip is not inserted, but instead provides an emergency eye wash (flushing) system.

Eye flushing systems are used to remove contaminants from an eye or the eyes of an individual. Typically, these systems are not portable, and are rather large. For this reason, they are typically unavailable at many locations where they would be useful.

This alternative embodiment is a portable eye flushing system 50 which replaces the irrigation tip 16 with a flushing adapter. The eye flushing system 50 is comprised of the cap adapter 12, the curved tube 14, and a flushing cup 52. The container of fluid 54 is also needed for the system to work, but is not considered part of the system itself because any variety of containers can be substituted.

As shown in FIG. 8A, the fluid container 54 is upended while the flushing cup 52 is pressed against (essentially around) the eye. This illustration shows the right eye being flushed. The flushing cup 52 includes an inlet port 56 and an exit port 58 for fluid to enter and exit therefrom. Pressure is exerted onto the sides of the fluid container 52 to cause the fluid therein to enter into the flushing cup 52 and wash out the eye.

FIG. 8B is provided as a top elevational view of the flushing cup 52. The curved tube 14 is coupled to the inlet port 56. Because the lip 60 of the flushing cup 52 is pressed against the skin around the eye, the exit port 58 provides a way for the fluid and contaminants to be flushed therefrom, thereby allowing continuous application of the fluid. It is also observed that the lip 60 is curved in such a way as to fit against the slope of a person's face around an eye. As shown in FIG. 8B, the flushing cup 52 is shown in a position which is correct for the right eye. Advantageously, it is a simple matter to simply twist the flushing cup 52 at the inlet port 56 and turn it over, making the system suitable for use on the left eye. However, it should also be apparent that the lip 60 does not have to be made in this manner. It is also possible to form the lip 60 in such a manner that use of the flushing cup 52 is possible on either eye without having to twist it. To compensate for the differences in the slopes of a person's face, a flexible seal can be disposed on the rim. For example, a flexible rubber can be disposed on the rim that is similar to a rubber rim found on the eyepieces of binoculars.

FIGS. 8C and 8D are provided as alternative views of the flushing cap 52 of FIG. 8B. Specifically, FIG. 8C is a side elevational view, and FIG. 8D is a side elevational view along the lines A—A shown in FIG. 8C.

Figure 9B:
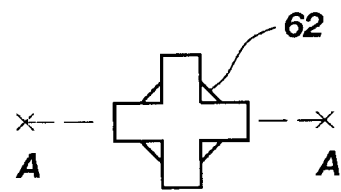
FIG. 9B is a close-up end view of the insertion end of FIG. 9A and shown along the lines A—A.
Figure 9A:
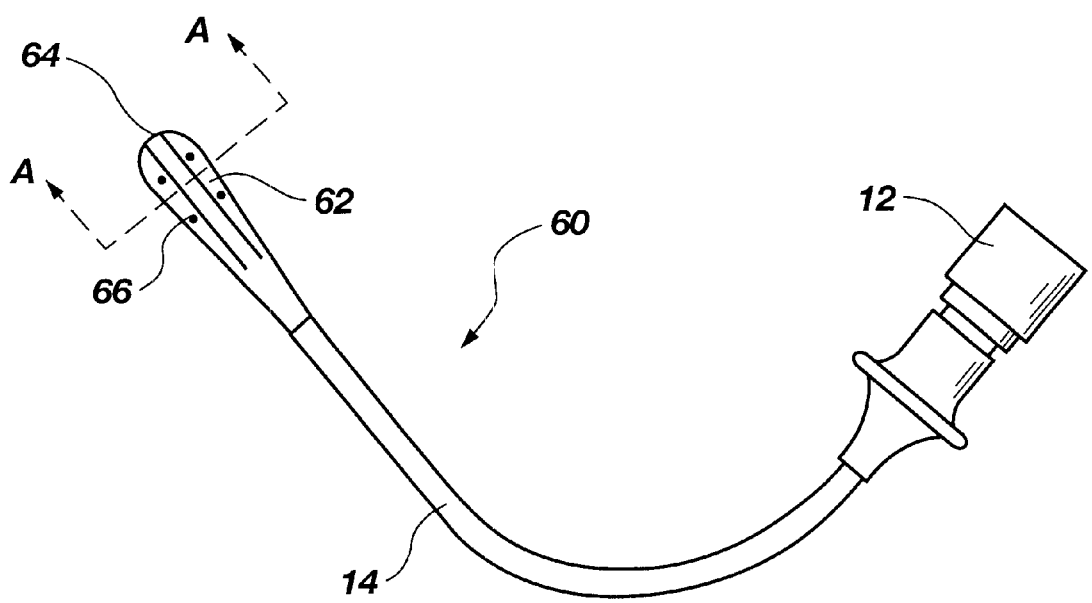
FIG. 9A is a side elevational view of the invention wherein the nasal insertion end is replaced by an end which is suitable for irrigation purposes as a feminine hygiene product.

FIG. 9A is provided to illustrate another alternative embodiment of the invention. In place of the irrigation tip 16 and the flushing cap 52, an insertion tip 62 is provided on the end of the flexible tube 14. This system 60 also includes the adapter cap 12.

The insertion tip 62 is specifically designed as an irrigation instrument for the purposes of feminine hygiene. The insertion tip 62 includes a smooth and rounded end 64, and a plurality of holes 66 along the sides of the insertion tip. These holes are for directing the fluid from an attached fluid container (not shown) and out of the insertion tip 62. As with the other embodiments, the nature of the materials used in construction enables the system 60 to be sterilized for repeated use.

FIG. 9B is provided as a view along the lines A—A of FIG. 9A. It should be apparent that the specific shape of the insertion tip 62 can vary. It only needs to be capable of easy insertion and withdrawal, be sterilizable, and capable of directing fluid out of the sides thereof.

Figure 10B:
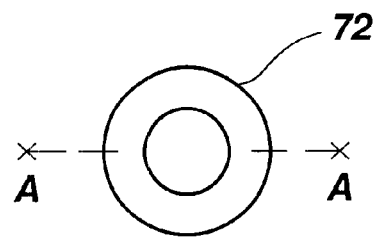
FIG. 10B is an end view of the object in FIG. 10A, and shown along lines A—A.
Figure 10A:
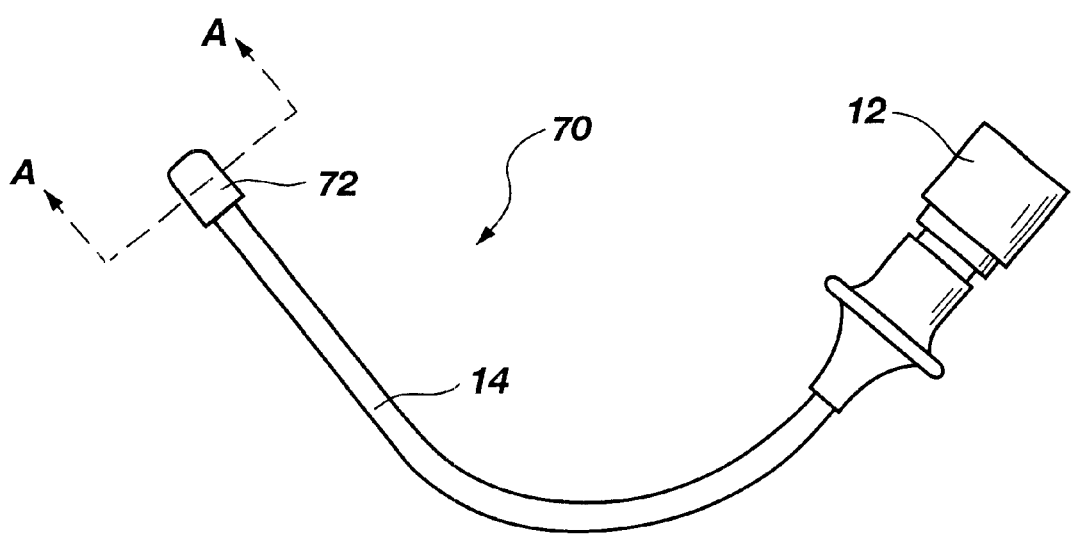
FIG. 10A is a side elevational view of the invention where the nasal insertion end is replaced by an end which is suitable for delivering fluid to a person whose mouth is partially obstructed by headgear, thereby facilitating delivery of a fluid to the person without having to remove the headgear.

FIG. 10A is provided to illustrate another alternative embodiment of the invention. In place of the irrigation tip 16 and the flushing cap 52, a drink dispensing tip 72 is provided on the end of the flexible tube 14. This system 70 also includes the adapter cap 12.

The drink dispensing tip 72 is specifically designed to deliver a drink to a person who is wearing headgear or other apparatus which makes it difficult to drink. For example, some football helmets include a face mask which prohibits the use of a cup when drinking. This alternative embodiment provides a drink dispensing tip 72 which can pass through such a face mask and enable drinking therefrom.

FIG. 10B is provided as a view along the lines A—A of FIG. 10A. It should be apparent that the specific shape of the drink dispensing tip 72 can vary. It only needs to be capable of fitting around headgear which otherwise prevents a person from using a cup to drink.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A portable fluid delivery system for delivering a fluid to a desired location by attaching the system to a portable fluid source, wherein the system is comprised of:

an adapter cap having a coupling end and a delivery end, wherein the coupling end is adapted for insertion over a sports cap which has a cap stopper removed, and wherein there is a first injection aperture extending from the coupling end to the delivery end;

a sports cap coupled in sliding engagement with the adapter cap, wherein the sports cap is formed with screw threads for attachment to corresponding screw threads of a fluid container;

an injection tip having an injection end and a coupling end, wherein there is a second injection aperture extending through the injection tip from the coupling end to the injection end; and a connecting tube which is coupled to the first injection aperture and the second injection aperture such that fluid received at the adapter cap will flow from the adapter cap to the injection tip for injection into the nasal passages and sinus cavities.

2. The portable fluid delivery system as described in claim 1 wherein the system is used to delivery fluid to a nasal passage or cavity, wherein the injection tip further comprises an insertion barrier which is disposed about the injection tip at a predetermined distance from an end thereof, thereby preventing insertion of the injection tip into the nasal passage beyond the insertion barrier when irrigating.

3. The portable fluid delivery system as described in claim 2 wherein the insertion barrier further comprises an ellipsoid extending outwards in a ring around the insertion barrier.

4. The portable fluid delivery system as described in claim 2 wherein the injection tip further comprises a gradual slope from the end of the injection tip, to an outer edge of the insertion barrier, to thereby prevent injury to the nasal passage from sharp edges.

5. The portable fluid delivery system as described in claim 1 wherein the coupling end of the adapter cap further comprises a plurality of ridges on an interior thereof, whereby the adapter cap is coupled in sliding engagement with the sports cap, and wherein in a non-extended state the adapter cap prevents fluid flow therethrough, and in an extended state the adapter cap enables fluid flow therethrough.

6. The portable fluid delivery system as described in claim 1 wherein the connecting tube further comprises the connecting tube being bent at an angle which is at least 120 degrees and being formed as a gradual bend therein, without any corners in the connecting tube.

7. The portable fluid delivery system as described in claim 6 wherein the portable fluid delivery system further comprises the connecting tube being disposed in sliding engagement with the adapter cap and the injection tip, wherein the connecting tube is partially disposed within the first injection aperture and the second injection aperture.

8. The portable fluid delivery system as described in claim 6 wherein the connecting tube further comprises being bent at an angle between 45 degrees and 90 degrees.

9. The portable fluid delivery system as described in claim 1 wherein the portable fluid delivery system further comprises being constructed of plastics selected from the group of plastics consisting of polyproplynen, polyethylene, and medical grade plastics.

10. The portable fluid delivery system as defined in claim 1 wherein the system is adapted for flushing a contaminant from an eye, said injection tip being replaced by an eye flushing cap having an inlet port and an outlet port, wherein the inlet port receives a fluid and the outlet port enables exit of fluid from the eye flushing cap when the cap is being held against a person's face, and wherein the connecting tube which is coupled to the first injection aperture is also coupled to the inlet port such that fluid received at the adapter cap will flow from the adapter cap to the eye flushing cap so as to wash the eye, and exit the eye flushing cap through the outlet port.

11. The portable fluid delivery system as defined in claim 1 wherein the system is adapted to function as a feminine hygiene system for delivering a medicinal or cleansing agent in a fluid to a body part or cavity for medicinal or hygienic purposes, said injection tip being replaced by an elongated and rounded injection end having a plurality of injection holes therethrough to thereby enable a fluid to pass through the injection end and into the body part or cavity.

12. The portable fluid delivery system as defined in claim 1 wherein the system is adapted to function as a drinking fluid delivery system for delivering a consumable fluid to a person's mouth, said injection tip being removed and replaced by a covering for an end of the connecting tube to thereby cover any sharp edges located thereon, such that the connecting tube is inserted into the person's mouth to obtain the consumable fluid.

13. A nasal irrigation system for delivering a fluid to tissue of nasal passages and sinus cavities, wherein the system is comprised of:

a sports cap having a coupling end and a delivery end, wherein the coupling end includes screw threads which couple to corresponding screw threads on a fluid container;

an adapter cap having a coupling end and a delivery end, wherein the coupling end is adapted for sliding engagement with the sports cap, and wherein there is a first injection aperture extending from the coupling end to the delivery end;

an injection tip having an injection end for and a coupling end, wherein there is a second injection aperture extending through the injection tip from the coupling end to the injection end; and a connecting tube which is coupled to the first injection aperture and the second injection aperture such that fluid received at the adapter cap will flow from the adapter cap to the injection tip for injection into the nasal passages and sinus cavities, and wherein the connecting tube is bent at an angle which is at least 120 degrees.

14. A method for delivering a fluid to tissue of nasal passages and sinus cavities by using a nasal irrigation system, wherein the method comprises the steps of:

(1) providing an irrigation system including a sports cap coupled in sliding engagement with an adapter cap, the sports cap formed with screw threads for attachment to corresponding threads of a fluid container, an injection tip for injecting the fluid, and a connecting tube which is coupled between and directs fluid from the adapter cap and the injection tip, and wherein the connecting tube is bent at an angle of at least 120 degrees;

(2) coupling the irrigation system to the fluid container which holds a sterile solution;

(3) turning over the fluid container to thereby direct the injection tip into a nostril; and (4) applying pressure to the fluid container to thereby force the sterile solution from the fluid container, through the adapter cap, the connecting tube and the injection tip and into the nasal passages and sinus cavities.

15. The method as described in claim 14 wherein the method further comprises the step of providing an insertion barrier about the injection tip at a predetermined distance from an end thereof, thereby preventing insertion of the injection tip into a nasal passage beyond the insertion barrier.

16. The method as described in claim 15 wherein the method further comprises the step of eliminating sharp edges between the insertion tip and the insertion barrier by providing a gradual slope therebetween, thereby preventing injury to tissue.

17. The method as described in claim 14 wherein the method further comprises the step of providing a means for closing the irrigation system to thereby prevent the flow of fluid from the fluid container when not in use.

18. The method as described in claim 14 wherein the method further comprises the step of angling the connecting tube such that a user must hold the fluid container in an up-ended position to thereby facilitate forcing the fluid from the fluid container and into the nasal passages and sinus cavities.

19. The method as described in claim 14 wherein the method further comprises the step of replacing the injection tip with a second injection tip having a different configuration to thereby adapt the irrigation system to direct fluid in a different manner.

20. The method as described in claim 14 wherein the method further comprises the step of constructing the irrigation system from materials that can be sterilized for reuse.

* * * * *